US00PP07817P

United States Patent [19]

Van Andel

[11] Patent Number: Plant 7,817

[45] Date of Patent: Mar. 3, 1992

[54] CARNATION NAMED 'STABAROSE'

[75] Inventor: Jacob Van Andel, Aalsmeer, Netherlands

[73] Assignee: Van Staaveren B.V., Aalsmeer, Netherlands

[21] Appl. No.: 549,801

[22] Filed: Jul. 9, 1990

[51] Int. Cl.[5] ..... A01H 5/00

[52] U.S. Cl. ..... Plt./71

[58] Field of Search ..... Plt./71, 70, 72

*Primary Examiner*—Howard J. Locker

[57] ABSTRACT

A new and original mini-spray carnation variety particularly distinguished by the Neyron Rose coloration of its small sized blossoms, which are produced intermittently during the Spring, Summer, and Fall blooming periods; the plant itself has a vigorous and upright growth habit and a height of about 60 cm.

1 Drawing Sheet

BACKGROUND OF THE NEW PLANT

This new mini-spray carnation cultivar originated as a hybrid seedling developed by me in 1980 at our nursery in Aalsmeer, Holland by crossing two varieties selected from our collection of carnations maintained for breeding purposes at Aalsmeer. This particular seedling was selected for propagation because of its unusual Neyron Rose coloration and the overall high quality of its growth. Asexual propagation of this selected plant was done by means of cuttings under my direction at Aalsmeer. Propagation of this new plant by cuttings continued from generation to generation to determine whether the novel characteristics of the selected seedling would be retained from generation to generation and its homogeneity could be assured. This proved to be successful and this new mini-spray carnation variety is now being propagated at Aalsmeer.

DESCRIPTION OF THE DRAWING

My new mini-spray carnation cultivar is illustrated by the accompanying photographic drawing, which shows blooming portions of spray stems with buds and flowers in several stages of development, the color rendition being as nearly true to that herein specified as is reasonably possible to obtain by professional photographic procedures.

DESCRIPTION OF THE NEW PLANT

The following is a detailed description of my new mini-spray carnation variety based upon observation of plants grown in greenhouse as well as outdoors at Aalsmeer and blooming during the current year. The color designations stated herein are according to The R.H.S. Colour Chart published by The Royal Horticultural Society of London, England.

THE PLANT

Origin: Seedling.
Parentage:
- *Seed parent.*—86239-1A (unpatented).
- *Pollen parent.*—*D. barbatus* (unpatented).

Classification:
- *Botanic.*—Dianthus hybrid.
- *Commercial.*—Mini-spray carnation.

Form: Strong bush with hardly any shoots at the flower stem nodes.

Height: 60 cm, in average.
Main stem:
- *length.*—In average, about 50 cm.
- *Growth.*—Vigorous and strong.
- *Branching character.*—Hardly any shoots in the flower stem nodes.

Foliage:
- *Number of leaves.*—Varies with season or amount of daylight.
- *Leaf size.*—About 165 mm long and 20 mm wide at the fifth node.
- *Leaf shape.*—Elliptical, curled and pointed. Margins: Entire. Texture: Leathery. Color: Both upper and under side are dark green.

THE BUD

Size: Small.
- *Diameter.*—Averaging about 10 mm.
- *Length.*—Averaging about 20 mm.

Shape: Ovoid.
Calyx:
- *Shape.*—Cylindrical.
- *Size.*—Averaging about 10 mm in width and 20 mm in length.
- *Splitting.*—The calyx does not split.
- *Aspect.*—Smooth.

Flower stem:
- *Character.*—Erect.
- *Color.*—Green.
- *Length.*—Averaging about 50 cm.

THE FLOWER

Blooming habit: Intermittent during normal blooming seasons.
Size of flower: Small.
- *Diameter.*—Averaging about 40 mm.
- *Depth.*—Averaging about 10 mm.

Borne: In a close, umbel-like cluster.
Shape:
- *When first opening.*—Flat.
- *When mature.*—High center.

Petalage:
- *Number of petals.*—Relatively few — about 18.
- *Texture.*—Soft.
  - *Appearance.*—Velvety.
- *Color.*—Both outer petals and inside petals: Body: 55 D. Base: White. Reverse Side: 55 C and 55 D.

Flower stem:

*Length.*—Averaging about 50 cm.

*Color.*—Green R.H.S. 137-B.

*Character.*—Strong and upright.

Discoloration after full bloom: In wet weather, color turns darker to R.H.S. 52 D.

Persistence: The flowers hang on and dry.

Disease resistance: Resistant to *Fusarium oxysporum.*

Lasting quality: Averaging about 14 days as a cut flower and 21 days on the plant.

REPRODUCTIVE ORGANS

Stamens:

*Number.*—Six.

*Arrangement.*—Petaloid rudimental.

*Anthers.*—Size: Small. Color: Pink/Violet. Filaments: Length: 5–20 mm, in average.

Pistils:

*Number.*—1.

*Styles.*—Length: About 25 mm. Color: White.

Stigmas:

*Color.*—Dark white.

I claim:

1. The new and distinctive carnation plant, substantially as herein shown and described, particularly characterized by its intermittent production of relatively small Neyron rose colored flowers borne in close umbel-like clusters on strong upright stems of a plant having a strong vigorous growth habit.

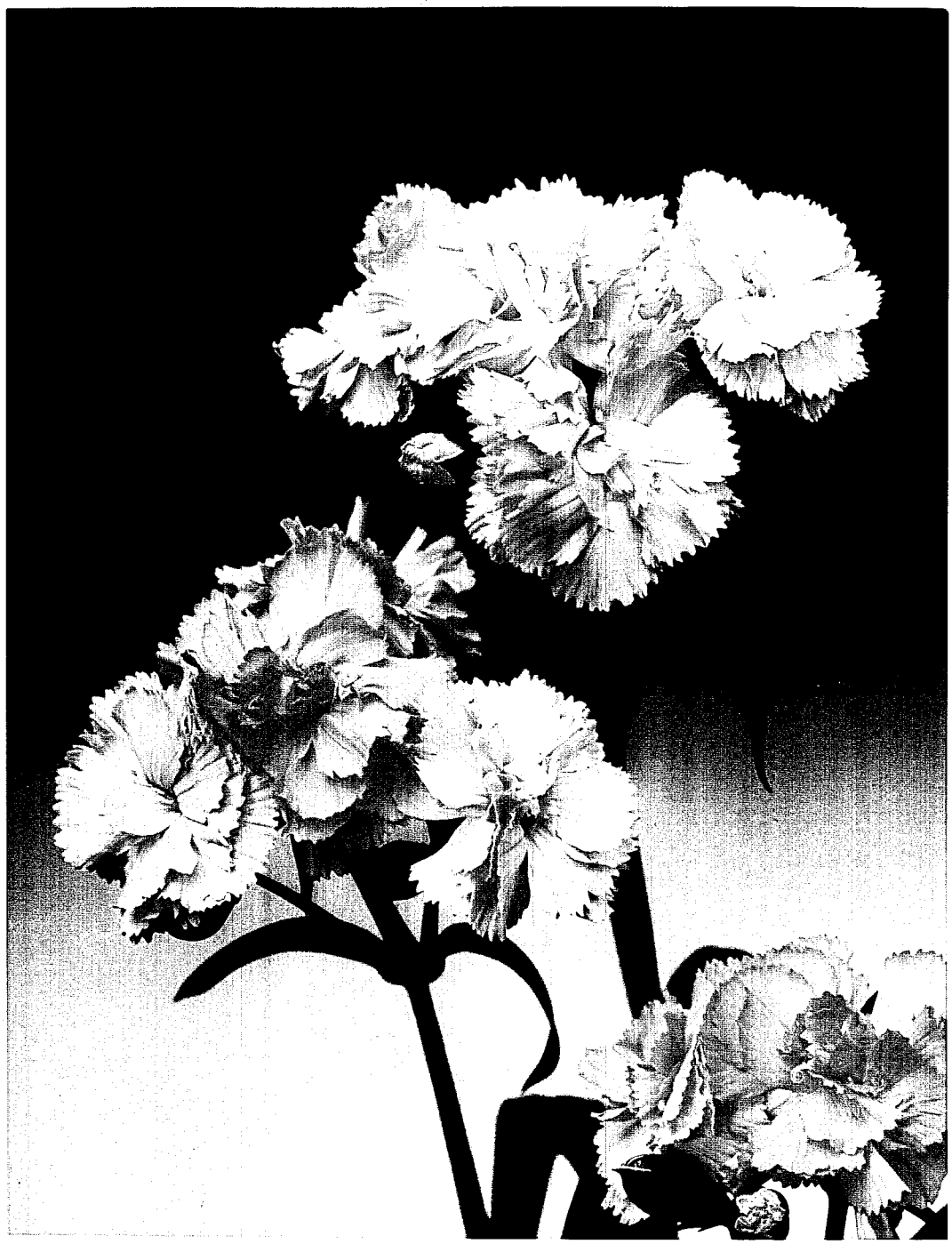

* * * * *